United States Patent [19]

Eisenberg et al.

[11] Patent Number: 4,669,481

[45] Date of Patent: Jun. 2, 1987

[54] METHOD OF MAGNETIC RESONANCE IMAGING USING CHROMIUM-LABELLED RED BLOOD CELLS

[75] Inventors: Alan D. Eisenberg; Thomas E. Conturo, both of Nashville; Chris J. Wehr, Brentwood; Mindy S. Schwartzberg, Nashville, all of Tenn.

[73] Assignee: Vanderbilt University, Nashville, Tenn.

[21] Appl. No.: 809,931

[22] Filed: Dec. 16, 1985

[51] Int. Cl.$^4$ .................. A61B 5/05; A61K 49/00
[52] U.S. Cl. ........................................ 128/654; 424/9
[58] Field of Search ............................ 128/653-654; 424/2, 4, 9; 436/173

[56] References Cited

U.S. PATENT DOCUMENTS 4,532,217  7/1985  Springer, Jr. et al. ......... 436/173 X
4,615,879 10/1986  Runge et al. .................. 128/653 X Primary Examiner—Kyle L. Howell
Assistant Examiner—Francis J. Jaworski
Attorney, Agent, or Firm—Tilton, Fallon, Lungmus & Chestnut

[57] ABSTRACT

Red blood cells (RBC's) loaded with nonradioactive chromium in paramagnetic form are employed as a contrast agent for magnetic resonance imaging (MRI). The method has promise for intravascular imaging applications where the contrast agent must remain in the circulatory system. Specific uses of this kind include locating gastrointestinal bleeding, differentiation of tumor from edema, MRI angiography, and determination of tissue perfusion. The Cr-labelled RBC's can also be used for liver and/or spleen MRI examinations.

8 Claims, No Drawings

METHOD OF MAGNETIC RESONANCE IMAGING USING CHROMIUM-LABELLED RED BLOOD CELLS

FIELD OF INVENTION, BACKGROUND, AND PRIOR ART

The field of this invention is contrast agents for magnetic resonance imaging (MRI). More specifically, this invention relates to intravascular contrast agents.

Magnetic resonance imaging has proven to be a very important imaging modality for diagnostic radiology. The high intrinsic contrast of living tissue available with MRI has allowed the radiologist to identify pathology which was previously unseen. However, MRI has its limitations. For example, MRI has been unable to evaluate organ function or perfusion, locate acute internal hemorrhage not associated with organ displacement, or distinguish a lesion (such as tumor) from surrounding edema.

Contrast agents are valuable in traditional radiologic methodologies. Following the advent of MRI, researchers began to investigate the use of contrast agents with this imaging modality. Animal research and preliminary human studies have demonstrated that contrast agents can increase the diagnostic capabilities of MRI.

Metal chelates, such as Gd-DTPA, and nitroxide stable free radicals (NSFRs) are two classes of MRI contrast agents currently receiving attention. These contrast agents have been found useful for certain MRI examinations. However, Gd-DPTA has a molecular weight of 590, and therefore is rapidly distributed throughout the extracellular fluid space. Brasch et al., AJR (1984) 143:215-224. Further, although Gd-DTPA acts as a marker of perfusion at 90 seconds postinfusion, it is not possible to utilize this property in vivo because of the lengthy scanning times MRI requires. See Wesbey et al., Radiology (1984) 153:165-169.

"TES," a piperidinyl NSFR derivative, is an example of the second class of MRI contrast agents currently being studied. However, like Gd-DTPA, TES is a small molecular weight compound and rapidly leaves the vascular compartment following intravenous injection. Brasch et al., Radiology (1983) 147: 773-779.

A proton magnetic resonance imaging contrast agent which remains for an appreciable time in the intravascular space is not presently available. Development of contrast agents specifically for the blood pool should markedly increase the clinical utility of MRI.

SUMMARY OF INVENTION

This invention is based in part on the discovery that red blood cells (RBC's) can be loaded with sufficient chromium to function effectively as intravascular MRI contrast agents. Chromium is known as a paramagnetic metal which is potentially useable as an MRI contrast agent. For example, it has been proposed to use chromium EDTA as an intravenous paramagnetic contrast agent. Runge et al., Radiology (1983) 147:789-791. As described by Runge et al., chromium is complexed with the chelating agent (EDTA) as the chromic ion ($Cr^{3+}$).

It has been known for many years that red blood cells will absorb chromate ions ($CrO_4^{-2}$) from aqueous solution. For use in nuclear medicine experiments and tests, radioactive chromium ($^{51}Cr$) has been introduced into RBC's in the form of its chromate ions. See, for example, Ebaugh et al., J. Clin. Invest. (1953) 32:1260-1276; and Donohue et al., Br. J. Haem. (1955) 1:259-263. The principal use of $^{51}Cr$-labelled RBC's in nuclear medicine has been to study erythrocyte survival, as described by Ebaugh et al., cited above. See, also, Wintrobe et al., "Clinical Hematology," (8TH ed., Philadelphia, Lea & Febiger, 1981), page 173.

When RBC's are tagged with radioactive chromium, only very small quantities of the $^{51}Cr$ label are required for the nuclear examinations. Prior to the present invention, it had not been suggested that sufficient nonradioactive chromium might be incorporated in RBC's so that the chromium-containing RBC's could be used as a contrast agent for MRI examinations. Coincidentally, and apparently unrecognized prior to the present invention, the chromium can be bound within RBC's in paramagnetic form, as needed for MRI use. More specifically, the hexavalent diamagnetic chromium in its chromate form ($Cr^{+6}$) is converted within the red cells to paramagnetic chromium ($Cr^{3+}$). The chromate form is required for penetration of the cell membranes of the RBC's, but fortuitously is converted to the $Cr^{+3}$ form which becomes bound to hemoglobin within the cells. Direct labelling with paramagnetic chromium would not be feasible since this $Cr^{+3}$ cation will not penetrate erythrocyte membranes.

In addition to its potential for locating hemorrhage, such as during acute gastrointestinal bleeding, the method of this invention is believed to be usable for many other kinds of MRI examinations. This method could provide a marker of perfusion allowing ischemic areas to be visualized as the absence of proton relaxation enhancement following contrast injection. Edematous tissue surrounding a highly vascularized tumor might be visualized by failure of the edema to enhance relative to the neoplasm. Further, relaxation enhancement of the circulatory system could provide a means of performing MRI angiography. Also, the method could facilitate the ability to measure flow with MRI by increasing the signal intensity of flowing blood.

Although the labeling process shortens the survival halftime of red cells in vivo, animal experiments have demonstrated that they remain in the circulation for approximately one week.

The RBC's could be deliberately damaged, such as by a mild heat treatment, before they are administered when it is desired to produce rapid reticuloendothelial segregation with resulting concentration of the paramagnetic chromium in the liver and spleen. The heat-treated RBC's would remain viable but be removed more rapidly by the reticuloendothelial system, thus providing an effective liver-spleen contrast agent.

DETAILED DESCRIPTION

In preparing nonradioactive paramagnetic chromium-labelled RBC's for use in the method of this invention, the RBC's are contacted with an aqueous chromate solution of specified chromate ion concentration. The concentration must be high enough to effectively label the RBC's being contacted without damaging the RBC's so that they become nonviable. Survival of the RBC's in the circulatory system is of importance. It has been found that the maximum concentration of the chromate ion in the labelling solution should be kept below a value at which appreciable hemolysis of the labelled RBC's will occur within a few hours.

For the purpose of certain examinations relating to the circulatory system, paramagnetic chromium-labelled RBC's should comprise an appreciable portion of the total RBC's in the patient's body. For example, in an MRI examination to locate the site of gastrointestinal bleeding, with present technology it is desirable to have the chromium-labelled RBC's comprise from 5 to 15% of the total RBC's in the circulatory system.

In practicing the method of this invention, it is necessary to obtain a supply of viable red blood cells (RBC's) administerable to a human patient prior to MRI examination. The RBC's may be obtained from the patient, such as by withdrawing a unit of blood (500 ml). Alternatively, or additionally, blood may be obtained from a blood bank and cross-matched to the patient's blood. For certain embodiments of the method, the amount of RBC's processed should correspond to about 5 to 15% of the patient's total RBC's. Usually about 1 unit of blood will be sufficient. For example, the RBC's in one blood unit (500 ml) roughly correspond to about 10% of a patient's RBC's. Significantly fewer labelled cells would be required for liver-spleen imaging utilizing heat damaged RBC's.

The RBC's are separated from the plasma and concentrated. High speed centrifugal separation is preferred. The RBC's are then contacted with an aqueous solution of chromate ions ($CrO_4^{-2}$). The solution may be prepared from chromate salts, such as sodium or potassium chromate. Sodium chromate is preferred, but the cation is noncritical, providing it is nontoxic and does not damage the RBC's.

It has been found that the initial chromate concentration of the solution for soaking the RBC's should be at least 1.0 millimolar (mM). The most effective concentrations are believed to be in the range of about 5 to 20 mM chromate. Higher concentrations can be used up to at least 25.0 mM chromate, but at concentrations of around 30.0 mM and above, the resulting chromium-labelled red blood cells may become unduly subject to hemolysis.

In preparing the solution for transferring the chromate to RBC's, sterile isotonic sodium chromate in ion-free water can be used. The mM concentration of Cr to which the RBC's are exposed is determined by the quantity of isotonic chromate solution added. Contact temperatures and times can be selected for effective chromate transfer while maintaining the viability of the RBC's. For example, temperatures ranging from 20° to 40° C. can be employed, and contact times of from 30 to 90 minutes. In one preferred procedure, the solution has a concentration of 10 mM sodium chromate, the incubation temperature is 37° C., the holding time about 1 hour.

After the RBC's have been loaded with chromate, they are separated from the aqueous solution. High speed centrifugal separation is the method of choice. The separated RBC's are washed to remove chromate from the exterior of the cells. Since chromate is a relatively toxic form of chromium, a series of washes may be employed. For example, the cells may be washed twice with normal saline, then with a solution of ascorbic acid, next with plasma, and finally two further washes with normal saline. The ascorbic acid wash is employed because the ascorbic acid will convert non-bound chromate to $Cr^{+3}$. For example, a typical concentration of the ascorbic acid wash is 10 mM.

The washed cells after separation of the final wash liquid, such as by centrifugation, are suspended in an intravascularly-administerable liquid carrier. Preferably, the RBC's are suspended in plasma.

The labelled RBC's in plasma may be handled and stored in the same manner as is done with blood in blood banks. The usual blood preservation additives may be used. Such procedures may include the use of citratephosphate dextrose (CPD). See Wintrobe, et al., "Clinical Hematology," (8th Ed., Philadelphia, Lea & Febiger, 1981), page 492. Refrigerated storage may be used, such as storage at about 4° C. It will usually be preferred to administer the chromium-labelled RBC's within a few hours after preparation, and usually not longer than 24 to 48 hours thereafter.

The Cr-labelled RBC's suspended in plasma or other suitable liquid carrier are administered to the patient by intravenous infusion. The same techniques and procedures can be followed as in the regular administration of blood. A typical time for administration of one unit (500 ml) is about 10 minutes. Depending on the particular MRI examination to be conducted, the patient may be examined immediately following the administration of the chromium-labelled RBC's, or an hour's delay may be required to permit heat damaged RBC's to reach certain targets.

For examinations of tissue perfusion only a short delay is required to permit the labelled RBC's to distribute themselves throughout the patient's blood. In carrying out an examination to locate the site of gastrointestinal bleeding, it should be sufficient to delay the examination for only about 20 to 60 minutes after the completion of the administration of the Cr-labelled RBC's. The length of delay is dependent upon the rate of hemorrhage, with slow or intermittent hemorrhage requiring a longer delay (hours) to allow accumulation of red cells in the GI tract. The patient's clinically suspected rate of hemorrhage (acute vs. subacute) would determine the optimal delay. For examinations of the liver and/or spleen, it will probably be desirable to delay the examination for about 1 hour, thereby permitting intentionally damaged labelled RBC's to be segregated by the reticuloendothelial system.

It is believed that RBC's labelled in accordance with the procedure described above are viable and relatively undamaged. Treating the labelled RBC's under mild heating conditions will damage the cells, resulting in rapid sequestration by the reticuloendothelial system. The cells can be specifically targeted for the spleen by heating for 10 minutes at 49° C. Greater temperature or length of heating produces increased cell damage, with resultant hepatic uptake. See Som et al., *Radiology*, (1981). Thus, if desired, the spleen or liver can be preferentially enhanced.

The MRI examination should be carried out in a known manner with respect to the particular purpose of the examination. In general, the pulse sequence will be selected to maximize either contrast induced changes in $T_1$ or $T_2$. $T_1$ and $T_2$ are tissue parameters which determine signal intensity in MR Imaging.

The method of the invention is further illustrated by the following experimental and practical examples.

EXPERIMENTAL EXAMPLES

$T_1$ and $T_2$ Measurements

Nonexpired, packed, citrate-anticoagulated human red blood cells (RBC's) were obtained from a blood bank. RBCs were incubated with various quantities of 103 millimolar (mM) $Na_2CrO_4$ ($Cr^{+6}$) at room temperature for 45 minutes, and then were washed 3 times to remove excess $Cr^{+6}$. Cells were packed after each washing by centrifugation at 4200 rpm for 5 minutes. A portion of each sample was diluted 10-fold with nonlabeled packed RBCs (9 parts unlabeled cells to 1 part labeled cells). Both diluted and undiluted samples were placed in test tubes for MR imaging, along with samples of non-labeled RBCs and 10 c mM $Na_2CrO_4$.

Two sets of tubes were imaged in the head coil (28 cm internal diameter) of a Technicare (Teslacon ®, Solon, Ohio), 0.5 tesla superconducting imaging system. A multiple spin echo (ME) sequence with echo times (TE) of 30, 60, 90, 120, 150, 180, 210 and 240 msec was repeated for repetition times (TR) of 300, 600, 1000, and 4000 mesc in order to generate sufficient data for $T_1$ and $T_2$ calculations. For each test tube and each TE and TR value the signal intensity and its standard deviation were collected with a 29-pixel region of interest. This size represents a region approximately one-third the cross-sectional area of each test tube, selected to avoid volume averaging along the tube's perimeter. $T_1$ and $T_2$ values were generated. Standard error of the mean (S.E.M.) was calculated.

Hemolysis

One ml of acid citrate dextrose (ACD) was added to each 10 ml sample of one of the phantoms postimaging prior to storage at 7° C., to maintain the physiologic state of the cells. Portions of RBC's were removed and washed at 2, 4, and 9 days postlabeling. The supernatants were measured for absorbance at 575 nm with a Varian Cary 210 spectrophotometer. Percent hemolysis was determined by dividing the absorbance of each sample by the absorbance of a sample of hemolized cells, then multiplying by 100.

Survival of Cr Labeled RBC's

Ten percent of the RBC mass of each of 6 New Zealand white rabbits were removed under sterile conditions and placed in vials containing ACD (1.5 ml ACD for each 10 ml of blood). The cells were incubated with Cr for 60 minutes at 37° C. Three rabbits were labeled with a small quantity of radioactive Cr, and functioned as controls. The remaining 3 rabbits were labeled with nonradioactive Cr at a concentration of 10 mM, to which had been added a small quantity of radioactive Cr. Post labeling the cells were washed in order to remove any nonbound Cr. The protocol entailed washing with equal quantities of normal saline twice, followed by 10 mM ascorbic acid (in saline), then plasma, and concluded with 2 additional saline washes. Following injection of the labeled cells, 1 ml samples of blood were removed from each rabbit daily for 3 days, and then every other day for a total of 3 weeks. The hematocrit of each sample was determined prior to counting in a Searle automatic gamma well counter with window settings for $^{51}Cr$. The number of counts were divided by the hematocrit to yield the net counts for each sample. The survival half time was computed by determining the time at which net counts had decreased to ½ that found shortly after injection of the labeled cells.

Organs Containing Labeled RBCs

Rabbits were anticoagulated with heparin prior to postmortem excision of both kidneys. The kidneys were flushed with heparinized iced saline through a catheter placed in the renal artery, and stored in a refrigerator until needed (6 hours maximum).

Packed human RBCs were optimally labeled as determined by the optimization study, by incubating at a Cr concentration of 10 mM for 60 minutes at 37°. Portions of labeled cells were diluted with nonlabeled cells as needed; and all samples were then diluted 2 parts RBCs to 1 part normal saline.

The kidneys were infused via the renal arterial catheter with suspensions of either all unlabeled cells, all labeled cells or 1 part labeled cells mixed with 9 parts unlabeled cells (10% labeled) as prepared above. The renal artery and vein were then simultaneously ligated in order to properly distend the intravascular space with red cells. The kidneys were placed in specimen containers and covered with gauze moistened with saline. The containers were packed in ice to maintain viability of the kidneys during MR imaging. Test tubes containing the RBCs used for infusion were positioned (in ice) in the imaging plane. Imaging and $T_1$ and $T_2$ calculation for the kidneys and tubes of blood were again performed as described above. The signal mean and standard deviations of the intensity of the entire kidney were collected.

RESULTS

1. $T_1$ and $T_2$ Measurements

The relaxation enhancement of packed RBCs labeled at various concentrations of Cr, for each of the 2 phantoms is shown in Tables A and B. It was observed that up to 3.16 mM, $T_1$ is a linear function of the quantity of Cr added to the blood during the labeling process. Above 3.16 mM the $T_1$ values appeared to level off. $T_2$ values decreased with increased Cr concentration.

$T_1$ and $T_2$ values of TBCs diluted 1 part labeled cells in 9 parts nonlabeled cells (Tables A and B). Over the entire range of Cr concentrations, the rate of change of the longitudinal and transverse relaxation rates ($1/T_1$, $1/T_2$) per unit change in Cr concentration were very similar. The relationship of $1/T_1$ and $1/T_2$ to Cr concentration is linear from 0.100 mM to 3.15 mM, with a steep slope indicating large changes in $T_1$ and $T_2$ with small changes in Cr concentration. Above 3.16 mM significantly less relaxation enhancement per unit Cr incubation concentration is obtained.

2. Hemolysis

Table C summarizes percent hemolysis at varying concentrations of Cr over time. Labeling with Cr at a concentration of 31.6 mM resulted in significant hemolysis by 2 days, and complete hemolysis 4 days postlabeling. Increased hemolysis over time occurred for all concentrations except 10 mM. The 10 mM sample had slightly greater hemolysis on days 2 and 9 than samples labeled at lower concentrations.

3. Survival of Cr Labeled RBC's

The survival half time of RBC's labeled with only a small quantity of radioactive Cr was 13.8 days. RBC's labeled at a Cr concentration of 10 mM were found to have a survival half time of 5.6 days. Please note that the normal life span of rabbit RBC's is approximately one-third that of human cells.

4. Organs Containing Labeled RBCs $T_1$ and $T_2$ values of rabbit kidneys containing labeled cells were obtained. A 20.2% (599.9—478.7/599.9×100) decrease in the $T_1$ of renal tissue containing only 10% labeled cells resulted. $T_2$ changes were less dramatic than $T_1$ changes, and in one instance paradoxically increased, although the general trend was toward decreasing $T_2$ values. In comparison, the $T_1$ of RBCs of which 10% had been Cr labeled represents a 28.5% (486.4-347.8/486.4×100) decrease as compared with nonlabeled cells.

TABLE A $T_1$ Values for Cr-Labelled RBC's

| Labelling Chromium Concentration (mM) | Study A | (S.E.) | Study B | (S.E.) | Mean | (S.E.) |
|---|---|---|---|---|---|---|
| $T_1$ (msec) for Undiluted Samples | | | | | | |
| 103 Cr$^{+6}$ | 2623.3 | (257.9) | 2153.2 | (176.9) | 2388.3 | (156.4) |
| 0 | 765.5 | (58.6) | 662.6 | (52.9) | 714.1 | (39.5) |
| 0.100 | 479.6 | (40.5) | 415.0 | (35.7) | 447.3 | (27.0) |
| 0.316 | 241.9 | (31.6) | 207.3 | (20.9) | 224.6 | (18.9) |
| 1.00 | 93.1 | (10.0) | 97.1 | (6.7) | 95.1 | (6.0) |
| 3.16 | 44.1 | (3.6) | 46.9 | (1.9) | 45.5 | (2.0) |
| 10.0 | ** | | 36.1 | (1.3) | 36.1 | (1.3) |
| 3.16 | * | | 33.1 | (2.0) | 33.1 | (2.0) |
| $T_1$ (msec) for Diluted (10%) Samples | | | | | | |
| 0.10 | 693.7 | (56.3) | 610.3 | (46.8) | 652.0 | (36.6) |
| 0.316 | 574.4 | (58.9) | 536.8 | (43.4) | 555.6 | (36.6) |
| 1.5 | 392.0 | (33.5) | 416.0 | (34.6) | 404.0 | (24.1) |
| 3.16 | 279.4 | (29.2) | 304.3 | (26.6) | 291.9 | (19.7) |
| 10.0 | 160.5 | (14.1) | 204.4 | (15.0) | 182.5 | (10.3) |
| 3.16 | * | | 87.6 | (4.0) | 87.6 | (4.0) |

*This sample was not included in Study A.
**The computer program was unable to generate a $T_1$ value for this sample.

TABLE B $T_2$ Values for Cr-Labelled RBC's

| Labelling Chromium Concentration (mM) | Study A | (S.E.) | Study B | (S.E.) | Mean | (S.E.) |
|---|---|---|---|---|---|---|
| $T_1$ (msec) for Undiluted Samples | | | | | | |
| 103 Cr$^{+6}$ | 615.4 | (119.1) | 517.8 | (81.9) | 566.6 | (72.3) |
| 0 | 140.2 | (8.5) | 92.9 | (3.9) | 116.6 | (4.7) |
| 0.100 | 134.7 | (6.9) | 104.1 | (4.4) | 119.5 | (4.1) |
| 0.316 | 100.7 | (5.2) | 84.3 | (3.1) | 92.5 | (3.0) |
| 1.00 | 64.0 | (2.1) | 51.0 | (1.0) | 57.7 | (1.2) |
| 3.16 | 29.2 | (0.8) | 29.4 | (0.4) | 29.3 | (0.4) |
| 10.0 | ** | | 25.4 | (0.3) | 25.4 | (0.3) |
| 31.6 | * | | 23.8 | (0.4) | 23.8 | (0.4) |
| $T_2$ (msec) for Diluted (10%) Samples | | | | | | |
| 0.100 | 151.3 | (9.1) | 100.1 | (4.1) | 125.7 | (5.0) |
| 0.316 | 145.8 | (9.8) | 95.5 | (3.8) | 120.7 | (5.3) |
| 1.00 | 139.0 | (7.2) | 94.6 | (3.6) | 116.8 | (4.0) |
| 3.16 | 107.8 | (5.1) | 86.9 | (3.0) | 97.4 | (3.0) |
| 10.0 | 101.2 | (3.4) | 66.5 | (1.9) | 83.9 | (1.9) |
| 3.16 | * | | 42.0 | (0.9) | 42.0 | (0.9) |

*This sample was not included in Study A.
**The computer program was unable to generate a $T_2$ value for this sample.

TABLE C

Hemolysis of Cr-Labelled RBC's

| Labelling Chromium Concentration (mM) | Percent Hemolysis | | |
|---|---|---|---|
| | Day 2 | Day 4 | Day 9 |
| 0 | * | 1.0 | 1.3 |
| 0.100 | 0.4 | 0.4 | 0.6 |
| 0.316 | 0.4 | 0.6 | 0.6 |
| 1.00 | 0.6 | 0.6 | 0.9 |
| 3.16 | 0.5 | 0.6 | 1.6 |
| 10.0 | 3.0 | 0.7 | 3.0 |
| 31.6 | 72.5 | Complete Hemolysis | |

*Not available.

PRACTICAL EXAMPLES

Clinical Applications

Clinical applications of the method of this invention can be illustrated with respect to (1) acute gastrointestinal hemorrhage and (2) liver and spleen imaging.

(1) Acute Gastrointestinal Hemorrhage

A patient is diagnosed clinically as having acute gastrointestinal (GI) hemorrhage by gross blood in the stool. The locaton of the bleeding must be determined so that his physicians can institute proper treatment. For example, if surgery is required, the surgeon must know where the bleeding site can be found.

The patient is probably already receiving cross-matched packed RBCs to replace those lost into the GI tract. A unit of packed cells is labeled with Cr at a concentration of 10 mM utilizing a FDA approved kit. The red cells are first transferred to a one-liter serum bag. The quantity of sterile isotonic sodium chromate solution required to label a unit of TBCs is supplied in a vial. The chromate solution is added to the red cells, mixed by inverting the bag, and placed in a 37° C. water bath. The cells are mixed approximately every 10 minutes for a total incubation of one hour.

Following incubation, 500 ml of sterile isotonic saline is added to the labeled cells. The cell suspension is mixed and centrifuged (in the bag) at approximately 3000 rpm for 10 minutes. After the supernatant is removed, 500 ml of saline is added to repeat the cell washing. The red cells are then washed with a 10 mM ascorbic acid solution and with cross-matched plasma. Finally, the cells are washed twice with saline.

Approximately 30 minutes prior to MR imaging the labeled RBCs are infused intravenously. Axial images are obtained with MRI through the abdominal region utilizing flow sensitive pulse sequences. The site of hemorrhage is identified by the presence of Cr labeled cells in the lumen of the GI tract. A region of abnormally high signal intensity will represent the bleeding site with a $T_1$ sensitive pulse sequence. The blood will appear as a region of abnormally low intensity utilizing a $T_2$ sensitive sequence.

(2) Liver and Spleen Imaging

Clinically a patient is suspected of having a lesion (tumor, abscess, etc.) in his liver which was not seen with non-contrasted MRI. A portion of the patient's blood volume (1–5%) is withdrawn into a sterile centrifuge tube containing ACD. The tube is centrifuged to remove the plasma from the RBCs. Sterile sodium chromate solution is added to the RBCs, mixed, and incubated at 37° C. for 60 minutes. Following incubation, the cells are washed as described above in the GI hemorrhage example, except that the volume of each wash is equal to the volume of cells being labeled, and the patient's own plasma (previously removed) is utilized for the plasma wash.

Prior to injection the labeled RBCs are heat damaged by exposure to 50° C. for 15 minutes. 30 to 60 minutes following intravenous infusion the liver is imaged with conventional pulse sequence techniques. The hepatic lesion is visualized by the absence of proton relaxation enhancement of the abnormal tissue.

We claim:

1. The method of magnetic resonance imaging (MRI) comprising the steps of:

(a) obtaining a supply of viable red blood cells (RBC's) administerable to a human patient;

(b) contacting the RBC's with an aqueous solution of chromate ions ($CrO_4^{-2}$) under conditions effective for transfer of the chromate ions into the RBC's, said solution having an initial chromate concentration of from 1.0 to 25.0 millimolar (mM);

(c) separating the chromium-containing RBC's from said aqueous solution;

(d) washing the separated RBC's to remove residual chromate exterior of the cells;

(e) suspending the washed RBC's in an intravascularly-administerable liquid carrier, said RBC's being in viable condition;

(f) introducing the suspended cells into the circulatory system of the patient; and, thereafter, (g) subjecting said patient to an MRI examination wherein the difference in the $T_1$ and/or $T_2$ values of the chromium-containing RBC's from the patient's normal RBC's provides an effective contrast for the examination.

2. The method of claim 1 in which the chromium-labelled RBC's at the time of said MRI examination comprise from 5 to 15% of the total RBC's in the patient's circulating system.

3. The method of claim 2 in which said examination is made to locate the site of gastrointestinal bleeding.

4. The method of claim 1 further comprising the step of heat damaging said RBC's prior to said introducing step so that the cells become segregated in the reticuloendothelial system, and said examination is of the liver and/or spleen.

5. The method of claim 1 in which said liquid carrier is plasma.

6. The method of claim 1 in which the said aqueous solution has an initial chromate concentration of 5 to 20 mM.

7. The method of magnetic resonance imaging (MRI) comprising the steps of:

(a) obtaining a supply of viable red blood cells (RBC's) administerable to a human patient, said supply corresponding to at least about 5 to 15% of the patient's total RBC's;

(b) contacting the RBC's with an aqueous solution of chromate ions ($CrO_4^{-2}$) under conditions effective for transfer of the chromate ions into the RBC's, said solution having an initial chromate concentration of from 5 to 20 millimolar (mM);

(c) separating the chromium-containing RBC's from said aqueous solution;

(d) washing the separated RBC's to remove residual chromate exterior of the cells;

(e) suspending the washed RBC's in plasma, said RBC's being in viable condition;

(f) introducing the suspended cells into the circulatory system of the patient, the amount of chromium-labelled RBC's introduced corresponding to from 5 to 15% of the total RBC's in the patient's circulatory system; and, thereafter, (g) subjecting said patient to an MRI examination wherein the difference in the $T_1$ and/or $T_2$ values of the chromium-containing RBC's from the patient's normal RBC's provides an effective contrast for the examination.

8. The method of claim 7 in which said examination is made to locate the site of gastrointestinal bleeding.

* * * * *